US010908063B2

(12) United States Patent
Gmira et al.

(10) Patent No.: US 10,908,063 B2
(45) Date of Patent: Feb. 2, 2021

(54) DYNAMICALLY DETERMINING A ROCK WETTABILITY ALTERATION

(71) Applicant: Saudi Arabian Oil Company, Dhahran (SA)

(72) Inventors: Ahmed Gmira, Al-Khobar (SA); Mohammed AlGeer, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/992,549

(22) Filed: Aug. 13, 2020

(65) Prior Publication Data

US 2020/0371010 A1    Nov. 26, 2020

Related U.S. Application Data

(62) Division of application No. 16/026,800, filed on Jul. 3, 2018.

(Continued)

(51) Int. Cl.
*G01N 15/08* (2006.01)
*G01N 33/24* (2006.01)
*G01N 13/02* (2006.01)

(52) U.S. Cl.
CPC .......... *G01N 15/082* (2013.01); *G01N 13/02* (2013.01); *G01N 33/24* (2013.01); *G01N 33/241* (2013.01); *G01N 2013/0208* (2013.01)

(58) Field of Classification Search
None
See application file for complete search history.

(56) References Cited

U.S. PATENT DOCUMENTS

| 4,688,938 A | 8/1987 | Demoulin et al. |
| 5,507,178 A | 4/1996 | Dam |

(Continued)

FOREIGN PATENT DOCUMENTS

| JP | 4563890 | 10/2010 |
| JP | 2017037080 | 2/2017 |
| WO | 2012140338 | 10/2012 |

OTHER PUBLICATIONS

Alshakhs et al., "Understanding the role of brine ionic composition on oil recovery by assessment of wettability from colloidal forces," Advances in Colloid and Interface Science, Elsevier, vol. 233, Aug. 20, 2015, 13 pages.

(Continued)

*Primary Examiner* — Paul M. West
*Assistant Examiner* — Mark A Shabman
(74) *Attorney, Agent, or Firm* — Fish & Richardson P.C.

(57) ABSTRACT

Techniques for determining a rock wettability alteration include circulating a first brine fluid into a test cell that includes a rock sample and a hydrocarbon fluid disposed on a surface of the rock sample, the first brine fluid having a property at a first value; contacting the rock sample and the hydrocarbon fluid with the first brine fluid; measuring a first contact angle between the rock sample and the hydrocarbon fluid in contact with the first brine fluid; at least partially displacing the first brine fluid with a second brine fluid in the test cell, the second brine fluid having the property at a second value; contacting the rock sample and the hydrocarbon fluid with the second brine fluid; measuring a second contact angle between the rock sample and the hydrocarbon fluid in contact with the second brine fluid; and determining a wettability alteration of the rock sample based on at least one of the measured first or second contact angles.

20 Claims, 4 Drawing Sheets

Related U.S. Application Data (60) Provisional application No. 62/563,739, filed on Sep. 27, 2017.

(56) References Cited

U.S. PATENT DOCUMENTS

| | | | |
|---|---|---|---|
| 5,861,946 A | 1/1999 | Hudson et al. | |
| 6,982,787 B1 | 1/2006 | Wapner et al. | |
| 8,474,306 B1* | 7/2013 | Behroozi | G01N 13/02 |
| | | | 73/64.52 |
| 8,768,628 B2* | 7/2014 | Ghedan | G01N 33/24 |
| | | | 702/12 |
| 9,016,111 B2 | 4/2015 | Stukan et al. | |
| 9,086,354 B2 | 7/2015 | AlSahan et al. | |
| 9,581,527 B2 | 2/2017 | Leck | |
| 9,675,994 B2 | 6/2017 | Schoenfisch | |
| 2005/0212869 A1 | 9/2005 | Ellson | |
| 2012/0181019 A1 | 7/2012 | Saini et al. | |
| 2013/0152668 A1 | 6/2013 | Stukan et al. | |
| 2014/0147627 A1* | 5/2014 | Aizenberg | A61L 33/064 |
| | | | 428/141 |
| 2014/0147631 A1 | 5/2014 | Yang | |
| 2015/0211973 A1 | 7/2015 | Friedrich et al. | |
| 2015/0233223 A1 | 8/2015 | AlAmeri et al. | |
| 2015/0259754 A1 | 9/2015 | Kaler | |
| 2016/0272873 A1 | 9/2016 | Mahadevan et al. | |
| 2016/0339424 A1 | 11/2016 | Megaridis | |
| 2017/0028330 A1 | 2/2017 | Dawar | |
| 2017/0030819 A1* | 2/2017 | McCarty | C09K 8/605 |
| 2019/0094120 A1 | 3/2019 | Gmira et al. | |
| 2019/0242803 A1 | 8/2019 | AlGeer et al. | |

OTHER PUBLICATIONS

Alshakhs, "An Experimental Study of the Impact of Injection Water Composition on Oil Recovery from Carbonate Rocks," A Dissertation Submitted to the Department of Energy Resources Engineering and the Committee on Graduate Studies of Stanford University in Partial Fulfillment of the Requirements for the Degree of Doctor of Philosophy, Jun. 2015, 171 pages.

Alshehri, "An X-Ray CT Study of Multidimensional Imbibition in Dual Porosity Carbonates," A Dissertation submitted to the Department of Energy Resources Engineering and the Committee on Graduate Studies of Stanford University in Partial Fulfillment of the Requirements for the Degree of Doctor of Philosophy, Oct. 2013, 434 pages.

Attension, "Static and dynamic contact angles and their measurement techniques," Biolin Scientific, available on or before Aug. 2017, 3 pages.

Dyne Testing, "Contact Angle Measurement Equipment," Dyne Testing Ltd, available on or before Dec. 26, 2016, 2 pages.

Extrand and Yumagai, "An experimental study of contact angle hysteresis," Journal of Colloid and Interface Science vol. 191, Apr. 18, 1997, 7 pages.

Extrand and Yumagai, "Contact angles and hysteresis on soft surfaces," Journal of Colloid and Interface Science vol. 184, Jul. 16, 1996, 11 pages.

Kruss, "Comparison of Wilhelmy and Sessile Drop Technique: A practical comparison of the techniques used to measure contact angles for liquids on non-porous solids," 1996 Annual Meeting of the Society of Tribologists and Lubrication Engineers, Lubrication Engineering, Tribology Transactions, Jan. 1996, 4 pages.

Kruss, "Drop Shape Analyzer—DSA100," Kruss: Advancing your Surface Science, available on or before Aug. 22, 2017, retrieved from URL <https://www.kruss-scientific.com/products/contact-angle/dsa100/drop-shape-analyzer-dsa100e/>, 8 pages.

Kruss, "Drop Shape Analyzer—DSA25," Kruss: Advancing your Surface Science, available on or before Aug. 22, 2017, retrieved from URL <https://www.kruss-scientific.com/products/contact-angle/dsa25/drop-shape-analyzer-dsa25/>, 4 pages.

Kruss, "Drop Shape Analyzer—DSA30," Kruss: Advancing your Surface Science, available on or before Jun. 2014, 4 pages.

Kruss-Scientific.com [online], "Advancing Angle," available on or before Aug. 21, 2017, retrieved from URL<https://www.kruss.de/services/education-theory/glossary/advancing-angle/>, 1 page.

Lamour et al., "Contact Angle measurements using a simplified experimental set-up," Journal of Chemical Education, vol. 87, No. 12, Dec. 2010, 5 pages.

MacDougall and Ockrent, "Surface energy relations in liquid/solid systems I. The adhesion of liquids to solids and a new method of determining the surface tension of liquids," Proceedings of the Royal Society of Medicine of London, vol. 180, Jun. 5, 1942, 23 pages.

Mahani et al., "Kinetics of the Low Salinity Watefflooding Effect Studied in a Model System," SPE Enhanced Oil Recovery Conference, Jul. 2, 2013, 14 pages.

Rao "Measurements of dynamic contact angles in solid-liquid-liquid systems at elevated pressures and temperatures," Colloids and Surfaces A: Physiochemical and Engineering Aspects, vol. 206, No. 1-3, Jul. 1, 2002, 14 pages.

Rao, "Correlation of Oil-Water Flow Behavior in Reservoir Rocks with Dynamic Contact Angles," Journal of Canadian Petroleum Technology, vol. 41, No. 7, Jul. 2002, 8 pages.

Roberts et al., "Ultrasonic Removal of Organic Deposits and Polymer Induced Formation Damage," SPE Formation Damage Control Symposium, Feb. 14-15, 1996, 9 pages.

Shedid and Ghannam, "Factors affecting contact-angle measurement of reservoir rocks," Journal of Petroleum Science and Engineering, vol. 44, Nov. 2004, 12 pages.

Vinci Technologies, "Interfacial Tension Measurements with IFT 700," Vinci Technologies, available on or before May 2010, 5 pages.

Yousef et al., "The Impact of the Injection Water Chemistry on Oil Recovery from Carbonate Reservoirs," SPE—154077, presented at the SPE EOR Conference at Oil and Gas West Asia, Apr. 16-18, 2012, 14 pages.

Yuan and Lee, "Contact angle and wetting properties," Springer Verlag Berlin Heidelberg, Springer Series in Surface Sciences, vol. 51, 2013, 33 pages.

GCC Examination Report in GCC Appln. No. GC 2018-36092, dated Feb. 3, 2020, 3 pages.

GCC Examination Report in GCC Appln. No. GC 2019-36979, dated Mar. 13, 2020, 4 pages.

GCC Examination Report in GCC Appln. No. GC 2019-36980, dated Mar. 27, 2020, 4 pages.

GCC Examination Report in GCC Appln. No. GC 2019-36092, dated Apr. 28 2020, 3 pages.

International Search Report and Written Opinion issued in International Application No. PCT/US2018/052434 dated Dec. 20, 2018, 13 pages.

International Search Report and Written Opinion issued in International Application No. PCT/US2019/015554 dated Apr. 9, 2019, 19 pages.

International Search Report and Written Opinion issued in International Application No. PCT/US2019/015758 dated Apr. 9, 2019, 16 pages.

\* cited by examiner

DYNAMICALLY DETERMINING A ROCK WETTABILITY ALTERATION

CROSS-REFERENCE TO RELATED APPLICATION

This application is a divisional of, and claims priority to, U.S. patent application Ser. No. 16/026,800, filed on Jul. 3, 2018, which in turn claims priority under 35 U.S.C. § 119 to U.S. Provisional Patent Application Ser. No. 62/563,739, filed on Sep. 27, 2017, and entitled "DYNAMICALLY DETERMINING A ROCK WETTABILITY ALTERATION." The entire contents of both previous applications are incorporated by reference herein.

TECHNICAL FIELD

The present disclosure relates to apparatus, systems, and methods for dynamically determining a rock wettability alteration.

BACKGROUND

Waterflooding with brine or seawater composition floods is often used for secondary recovery processes in hydrocarbon-bearing reservoirs. In some instances, waterflooding may alter a carbonate wettability of the rock formation in the reservoir, thereby affecting hydrocarbon production with the waterflood.

SUMMARY

In an example implementation, a method for determining a rock wettability alteration includes circulating a first brine fluid into a test cell that includes a rock sample and a hydrocarbon fluid disposed on a surface of the rock sample, the first brine fluid having a property at a first value; contacting the rock sample and the hydrocarbon fluid with the first brine fluid; measuring a first contact angle between the rock sample and the hydrocarbon fluid in contact with the first brine fluid; at least partially displacing the first brine fluid with a second brine fluid in the test cell, the second brine fluid having the property at a second value; contacting the rock sample and the hydrocarbon fluid with the second brine fluid; measuring a second contact angle between the rock sample and the hydrocarbon fluid in contact with the second brine fluid; and determining a wettability alteration of the rock sample based on at least one of the measured first or second contact angles.

In an aspect combinable with the general implementation, determining the wettability alteration of the rock sample based on at least one of the measured first or second contact angles includes determining the wettability of the rock sample based on the measured first contact angle and the measured second contact angle.

In another aspect combinable with any of the previous aspects, determining the wettability alteration of the rock sample based on the measured first contact angle and the measured second contact angle includes determining the wettability alteration of the rock sample based on a difference between the measured first contact angle and the measured second contact angle.

Another aspect combinable with any of the previous aspects further includes, while displacing the first brine fluid with the second brine fluid, circulating an output flow from the test cell, the output flow including one or both of the first brine fluid and the second brine fluid.

Another aspect combinable with any of the previous aspects further includes measuring a value of the property of the output flow while circulating the output flow from the test cell.

Another aspect combinable with any of the previous aspects further includes comparing the measured value of the property of the output flow with the second value of the property of the second brine fluid.

Another aspect combinable with any of the previous aspects further includes stopping the circulation of the output flow from the test cell when the measured value of the property of the output flow matches the second value of the property of the second brine fluid.

In another aspect combinable with any of the previous aspects, the property is conductivity.

In another aspect combinable with any of the previous aspects, the hydrocarbon fluid includes oil.

In another aspect combinable with any of the previous aspects, the first and second values are different.

Another aspect combinable with any of the previous aspects further includes at least partially displacing the second brine fluid with a third brine fluid in the test cell, the third brine fluid having the property at a third value; contacting the rock sample and the hydrocarbon fluid with the third brine fluid; measuring a third contact angle between the rock sample and the hydrocarbon fluid in contact with the third brine fluid; and determining the wettability alteration of the rock sample based on at least one of the measured first contact angle, the measured second contact angle, or the measured third contact angle.

In another aspect combinable with any of the previous aspects, determining the wettability alteration of the rock sample based on at least one of the measured first contact angle, the measured second contact angle, or the measured third contact angle includes determining the wettability of the rock sample based on the measured first contact angle, the measured second contact angle, and the measured third contact angle.

Another aspect combinable with any of the previous aspects further includes, while displacing the second brine fluid with the third brine fluid, circulating the output flow from the test cell, the output flow including one or both of the second brine fluid and the third brine fluid.

Another aspect combinable with any of the previous aspects further includes measuring a value of the property of the output flow while circulating the output flow from the test cell.

Another aspect combinable with any of the previous aspects further includes comparing the measured value of the property of the output flow with the third value of the property of the third brine fluid.

Another aspect combinable with any of the previous aspects further includes stopping the circulation of the output flow from the test cell when the measured value of the property of the output flow matches the third value of the property of the third brine fluid.

In another general implementation, a system includes a test cell configured to enclose a rock sample and a hydrocarbon fluid disposed on a surface of the rock sample; a first brine fluid tank configured to hold a volume of a first brine fluid, the first brine fluid having a property at a first value; a second brine fluid tank configured to hold a volume of a second brine fluid, the second brine fluid having the property at the second value; at least one pump fluidly coupled to the test cell and the first and second brine fluid tanks; and a control system communicably coupled to the pump. The control system is configured to perform operations including controlling the at least one pump to circulate the first brine fluid into the test cell to contact the rock sample and the hydrocarbon fluid with the first brine fluid; measuring a first contact angle between the rock sample and the hydrocarbon fluid in contact with the first brine fluid; controlling the at least one pump to circulate the second brine fluid into the test cell to displace at least a portion of the first brine fluid in the test cell and contact the rock sample and the hydrocarbon fluid with the second brine fluid; measuring a second contact angle between the rock sample and the hydrocarbon fluid in contact with the second brine fluid; and determining a wettability alteration of the rock sample based on at least one of the measured first contact angle or the measured second contact angle.

In an aspect combinable with the general implementation, the operation of determining the wettability alteration of the rock sample based on at least one of the measured first contact angle or the measured second contact angle includes determining the wettability of the rock sample based on the measured first contact angle and the measured second contact angle.

In another aspect combinable with any of the previous aspects, the operation of determining the wettability alteration of the rock sample based on the measured first contact angle and the measured second contact angle includes determining the wettability of the rock sample based on a difference between the measured first contact angle and the measured second contact angle.

Another aspect combinable with any of the previous aspects further includes, while displacing the first brine fluid with the second brine fluid, controlling at least one of the at least one pump or at least one valve to circulate an output flow from the test cell, the output flow including one or both of the first brine fluid and the second brine fluid.

In another aspect combinable with any of the previous aspects, the control system is configured to perform operations further including measuring a value of the property of the output flow while circulating the output flow from the test cell.

In another aspect combinable with any of the previous aspects, the control system is configured to perform operations further including comparing the measured value of the property of the output flow with the second value of the property of the second brine fluid.

In another aspect combinable with any of the previous aspects, the control system is configured to perform operations further including controlling at least one of the at least one pump or the at least one valve to stop the circulation of the output flow from the test cell when the measured value of the property of the output flow matches the second value of the property of the second brine fluid.

In another aspect combinable with any of the previous aspects, the property is conductivity.

In another aspect combinable with any of the previous aspects, the hydrocarbon fluid includes oil.

In another aspect combinable with any of the previous aspects, the first and second values are different.

Another aspect combinable with any of the previous aspects further includes a third brine fluid tank configured to hold a volume of a third brine fluid, the third brine fluid having the property at the third value.

In another aspect combinable with any of the previous aspects, the control system is configured to perform operations further including controlling the at least one pump to circulate the third brine fluid into the test cell to displace at least a portion of the second brine fluid in the test cell and contact the rock sample and the hydrocarbon fluid with the third brine fluid; measuring a third contact angle between the rock sample and the hydrocarbon fluid in contact with the third brine fluid; and determining the wettability alteration of the rock sample based on at least one of the measured first contact angle, the measured second contact angle, or the measured third contact angle.

In another aspect combinable with any of the previous aspects, the operation of determining the wettability alteration of the rock sample based on at least one of the measured first contact angle, the measured second contact angle, or the measured third contact angle includes determining the wettability of the rock sample based on the measured first contact angle, the measured second contact angle, and the measured third contact angle.

In another aspect combinable with any of the previous aspects, the control system is configured to perform operations further including, while displacing the second brine fluid with the third brine fluid, controlling at least one of the at least one pump or the at least one valve fluidly coupled to the test cell to circulate the output flow from the test cell, the output flow including one or both of the second brine fluid and the third brine fluid.

In another aspect combinable with any of the previous aspects, the control system is configured to perform operations further including measuring a value of the property of the output flow while circulating the output flow from the test cell.

In another aspect combinable with any of the previous aspects, the control system is configured to perform operations further including comparing the measured value of the property of the output flow with the third value of the property of the third brine fluid.

In another aspect combinable with any of the previous aspects, the control system is configured to perform operations further including controlling at least one of the at least one pump or the at least one valve to stop the circulation of the output flow from the test cell when the measured value of the property of the output flow matches the third value of the property of the third brine fluid.

Implementations according to the present disclosure may include one or more of the following features. For example, implementations of a contact angle measurement system may enable a realistic measurement of carbonates wettability alteration caused by salinity gradients and various determining parameters (for example, crude oil composition, reservoir pressure and temperature). Further, implementations of a contact angle measurement system may provide efficient measurements of a contact angle between crude oil and a carbonates rock surface while varying brine salinities in situ, thereby increasing an efficiency of experimental time management and decreasing a need for solvents used for crude oil cleaning. Implementations may better depict the wettability process in real reservoirs and eliminate uncertainty associated with multiple separate experimental tests used in conventional test systems. As another example, implementations of a contact angle measurement system may utilize a single test with a single rock surface while using multiple brine fluids (replaceable) in the test cell prior to the measurement, which are controlled by brine parameters such as salinity, conductivity, both, or other parameters. Further, implementations of a contact angle measurement system may provide a realistic emulation of salinity replacement in tertiary recovery, eliminate uncertainty due to multiple separate test runs, maximize experiment time management, and minimize solvents used for test cell and rock surface cleaning. As another example, implementations of a contact angle measurement system may provide depict an in-situ reservoir injected fluid sequence to better assess an impact of all enhanced oil recovery technologies that are dependent on wettability alteration as a mechanism to enhance oil recovery.

The details of one or more implementations of the subject matter described in this disclosure are set forth in the accompanying drawings and the description. Other features, aspects, and advantages of the subject matter will become apparent from the description, the drawings, and the claims.

DETAILED DESCRIPTION

The present disclosure describes implementations of systems and method for determining rock wettability. In some aspects, such implementations include an in☐situ dynamic measurement method to determine a salinity gradient effect on a contact angle between a hydrocarbon fluid (for example, crude oil) and a rock sample (for example, carbonates rock). Example implementations include a test cell that is used for contact angle measurements (for example, at standard conditions, high temperature/high pressure conditions, or both). In some aspects, in☐situ brine liquids may be circulated to the test cell to assess an impact of salinity gradient on oil recovery. In some aspects, the circulation of multiple brines (for example, serially) may be controlled by measuring a parameter of the brines (for example, conductivity) and using the measurement to control brine replacements inside the test cell. In some aspects, such implementations may enable a realistic measurement of carbonates wettability alteration caused by salinity gradient and various determining parameters (for example, crude oil composition, reservoir pressure and temperature, and other parameters).

Figure 1:
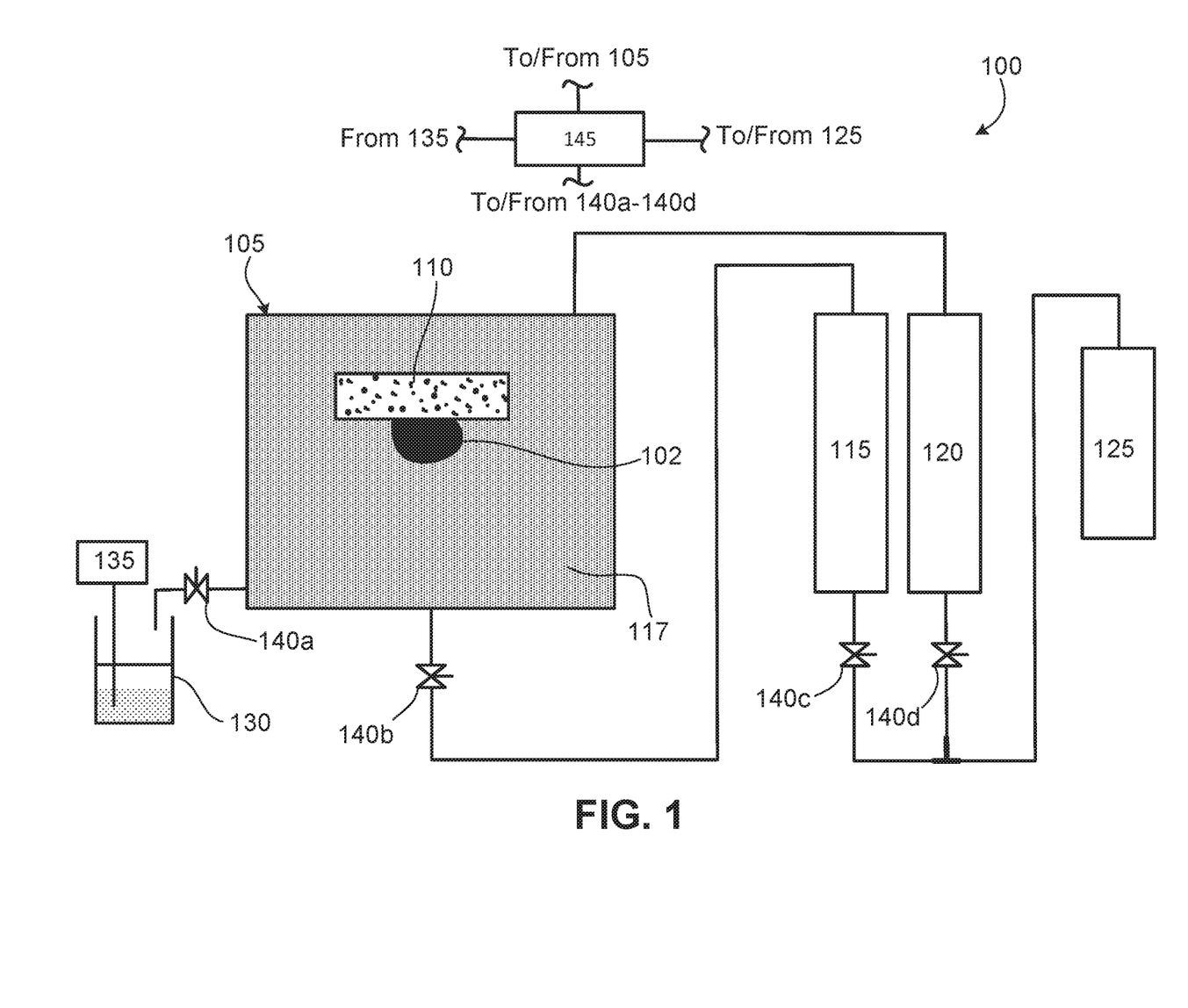
FIG. 1 is a schematic illustration of an example implementation of a contact angle measurement system according to the present disclosure.

FIG. 1 is a schematic illustration of an example implementation of a contact angle measurement system 100 ("system 100"). As shown, the system 100 includes a test cell 105 that encloses a rock sample 110 onto which a hydrocarbon fluid sample 102 is disposed (for example, on a surface of the rock sample 110). In some aspects, the rock sample 110 is or comprises a carbonates rock sample. In some aspects, the hydrocarbon fluid sample 102 is a crude oil sample (or other hydrocarbon liquid sample).

The test cell 105, in some aspects, may be a contact angle goniometer that is operable (for example, through imaging devices and a microprocessor based software system) to measure a static contact angle, as well as advancing and receding contact angles, between the hydrocarbon fluid sample 102 and the rock sample 110. In some aspects, the test cell 105 (for example, DSA100, KRUSS Gmbh or IFT-10, Corelab), as a contact angle goniometer, may also measure surface tension between the hydrocarbon fluid sample 102 and a brine liquid 107.

Figure 2A:
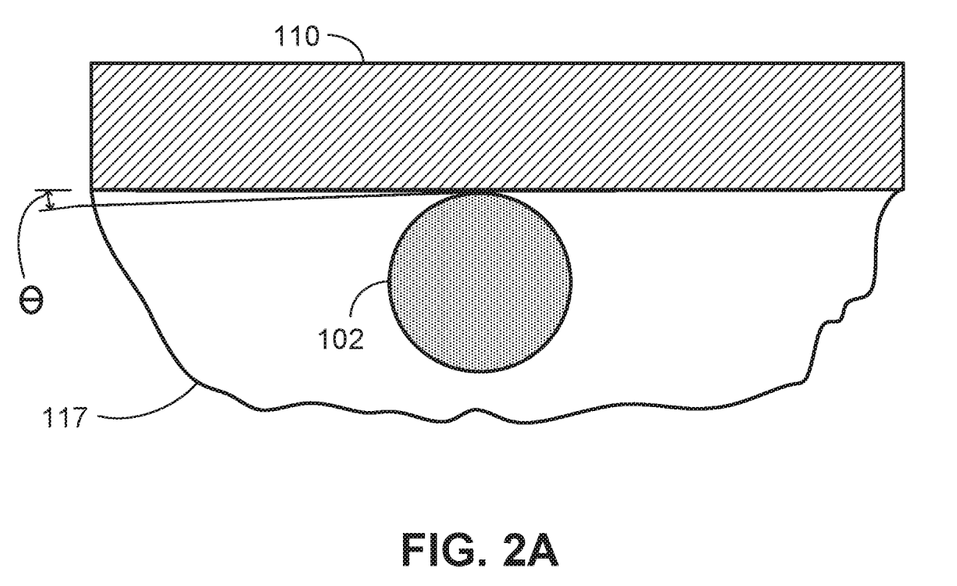
FIGS. 2A-2B show schematic illustrations of different contact angles between beads of hydrocarbon fluids on a rock surface.
Figure 2B:
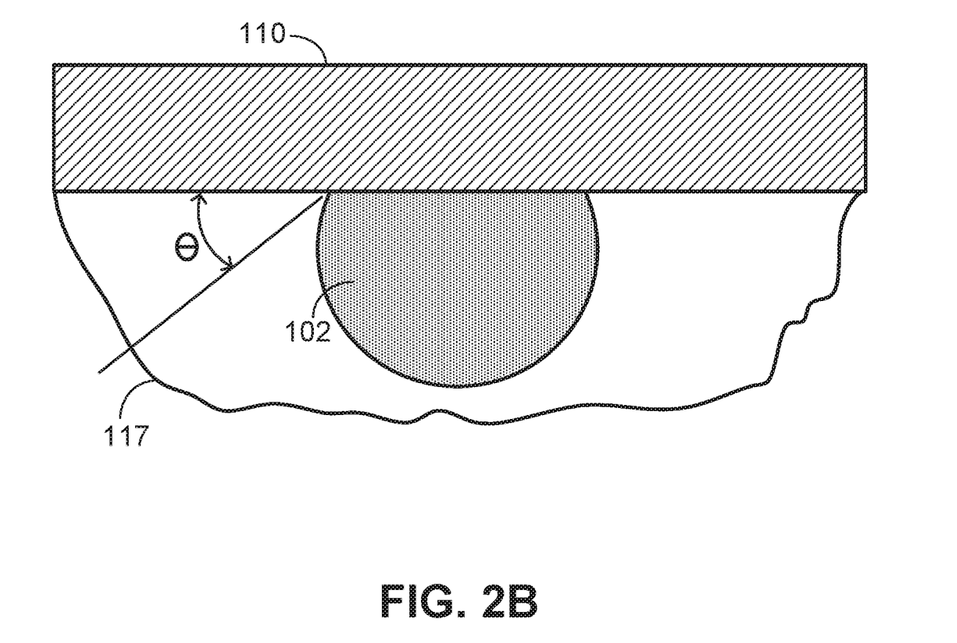

Turning briefly to FIGS. 2A-2B, these figures show schematic illustrations of different contact angles between beads of hydrocarbon fluid samples 102 on the rock sample 110. For example, in these figures, the symbol, Θ, represents a static contact angle between the hydrocarbon fluid sample 102 and the rock sample 110 surrounded by a brine liquid 117. The static contact angle, generally, is a measurement of where a liquid-vapor interface meets a solid surface; here, the liquid-vapor is the hydrocarbon fluid sample 102 while the solid surface is the rock sample 110. In some aspects, the contact angle quantifies the "wettability" of the solid surface according to the Young equation that relates interfacial energies (between solid-vapor, solid-liquid, liquid-vapor) to the static contact angle.

In the case of the wettability of hydrocarbon-bearing rocks, such as carbonates rocks, wettability indicates a preference for the rock to be in contact with a particular fluid (for example, hydrocarbon such as oil) over another particular fluid (for example, water, such as brine). Thus, the more preferred fluid would displace, on the rock surface, the less preferred fluid according to the wettability of the rock. Fluids that are not, or are little, preferred, form beads on the rock surface, while preferred fluids flatten, or spread, out on the rock surface. Rock formations are often referred to as "oil-wet" (meaning they have a preference for oil) or "water-wet" (meaning they have a preference for water). FIG. 2A shows an example of a "water-wet" rock sample 110, in that the hydrocarbon fluid sample 102 has beaded on the rock surface in the presence of the brine fluid 117. Here, the contact angle, Θ, is negligible (almost zero). FIG. 2B shows an example of a more "oil-wet" rock sample 110 as compared to FIG. 2A, in that the hydrocarbon fluid sample 102 has spread out on the rock surface in the presence of the brine fluid 117. Here, the contact angle, Θ, is larger. Fully "oil-wet" surfaces may have the hydrocarbon fluid sample 102 as nearly flat on the surface of the rock sample 110.

The wettability of a rock formation, in some aspects, may help determine an effectiveness of secondary or tertiary production processes, such as waterflooding. For example, waterflooding, generally, refers to the process of injecting water (or water-based liquid such as brine) into a reservoir to increase reservoir pressure and thereby increase hydrocarbon production. Thus, the wettability of a reservoir formation—whether such formation is water-wet or oil-wet—and how waterflooding can effect such wettability, as determined through contact angle measurement, may affect a choice or operation of stimulation.

Turning back to FIG. 1, the system 100 includes a hydrocarbon fluid sample tank 115 that is fluidly coupled to the test cell 105 though a valve 140b (for example, modulating or shut-off). Although shown as a single tank 115, there may be multiple different tanks 115 fluidly coupled to the test cell 105 through a single or multiple valves 140b. Each tank 115 may enclose a similar or different type of hydrocarbon fluid sample 102 (for example, crude oil of different weights).

As illustrated, the system 100 also includes a brine fluid tank 120 that is fluidly coupled to the test cell 105 (through or not through a valve, not shown). Although shown as a single tank 120, there may be multiple different tanks 120 fluidly coupled to the test cell 105 through a single or multiple valves. Each tank 120 may enclose a similar or different type of brine 117 (for example, each having a different salinity, different conductivity, or other property).

One or more pumps 125 is also fluidly connected to the tanks 115 and 120 and operable to circulate the hydrocarbon fluid sample 102, the brine fluid 117, or both, from the respective tanks 115 and 120. As illustrated, the pump 125 is fluidly connected to the tank (or tanks) 115 through valve (for example, modulating or shut-off) 140c, while the pump 125 is also fluidly connected to the tank (or tanks) 120 through valve (for example, modulating or shut-off) 140d.

As illustrated in FIG. 1, the system 100 also includes a drain valve 140a (for example, modulating or shut-off) that is fluidly coupled to an outlet of the test cell 105 and to an outlet tank 130 that receives an outlet flow of the brine fluid 117 in the test cell 105. A sensor 135 is positioned in the outlet tank 130 to measure one or more properties (or parameters), such as conductivity, or salinity of the brine fluid 117 that is circulated through the outlet valve 140a to the tank 130.

As shown, system 100 also includes a control system 145 (for example, microprocessor based, electromechanical, pneumatic, or other form of control system). As shown, the control system 145 is communicably coupled to send commands to, and receive information from, the pump (or pumps) 125. For example, the control system 145 may send commands to the pump(s) 125 to start or stop, or slow down or speed up, or both. The pump(s) 125 may send feedback to the control system 145, such as speed, flow rate, frequency, or a combination. In some aspects, the control system 145 may include or be controllably coupled to a variable frequency drive connected to the pump motor.

As shown, the control system 145 is also communicably coupled to send commands to, and receive information from, the valves 140a-140d. For example, the control system 145 may send commands to the valves 140a-140d to open fully or close fully, modulate toward open or modulate toward close. The valves 140a-140d may send feedback to the control system 145, such as status (open or close), percent open, or a combination.

As shown, the control system 145 is also communicably coupled to send commands to, and receive information from, the test cell 105. For example, the control system 145 may send commands to the test cell 105, such as, to measure a contact angle between the hydrocarbon fluid sample 102 and the rock sample 110. The test cell 105 may send feedback to the control system 145, such as the measured contact angle.

As shown, the control system 145 is also communicably coupled to receive information from the sensor 135. For example, the control system 145 may receive feedback from the sensor 135 in the form of a measured property or parameter of the brine fluid in the tank 130, such as salinity, conductivity, both, or other property.

Figure 3:
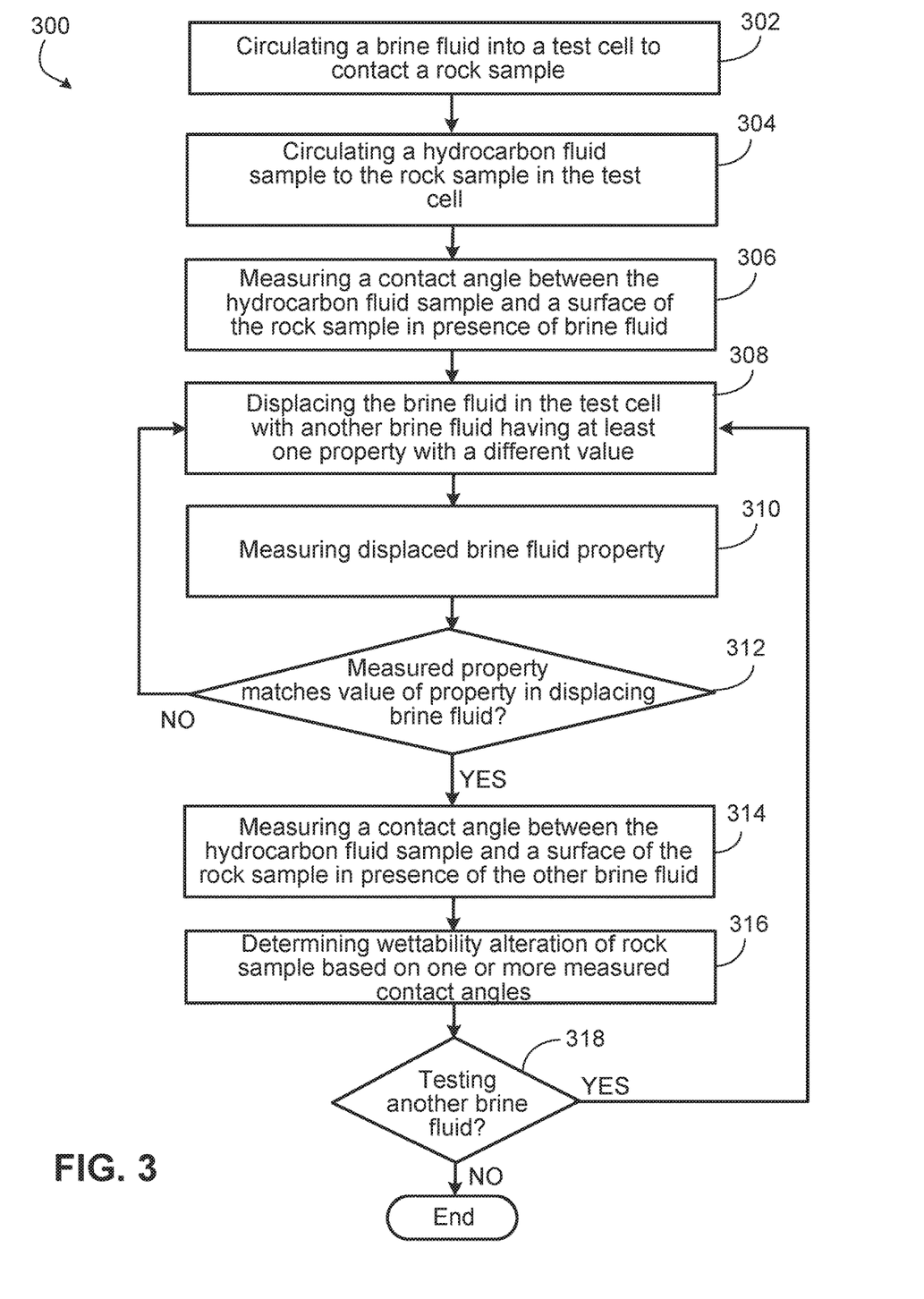
FIG. 3 is a flowchart that illustrates an example method for measuring a contact angle between a bead of hydrocarbon and a rock surface according to the present disclosure.

FIG. 3 is a flowchart that illustrates an example method 300 for measuring a contact angle between the hydrocarbon fluid sample 102 and the rock sample 110 with the system 100. In some aspects, by determining one or more contact angles between the hydrocarbon fluid sample 102 and the rock sample 110 in the presence of two or more different brine fluids 117, a wettability alteration of the rock sample 110 may be more accurately and easily determined in a single test set up with the test cell 105. Method 300 may begin at step 302, which includes circulating a brine fluid into the test cell to fill the cell and contact rock sample surface. For example, the control system 145 may close valves 140b and 140c, open valve 140d, and operate the pump 125 to circulate the brine fluid 117 into the test cell 105. In some aspects, the brine fluid may be a first of several brine fluids.

Method 300 may continue at step 304, which includes circulating a hydrocarbon fluid sample to a rock sample in a test cell. For example, as shown in FIG. 1, the control system 145 may close valve 140d, open valves 140b and 140c, and operate the pump 125 to circulate a sample of the hydrocarbon fluid (for example, crude oil) into the test cell 105 to be disposed on a surface of the rock sample 110.

Method 300 may continue at step 306, which includes measuring a contact angle between the hydrocarbon fluid sample and a surface of the rock sample in presence of the brine fluid (for example, the first brine fluid). For example, the test cell 105 (for example, as a contact angle goniometer) may measure a contact angle between the hydrocarbon fluid sample 102 disposed on the rock sample 110 and the surface of the sample 110 onto which the hydrocarbon fluid sample 102 is disposed.

Method 300 may continue at step 308, which includes displacing the brine fluid in the test cell with another brine fluid (for example, a second brine fluid) having at least one property with a different value that the displaced brine fluid. For example, once the contact angle has been measured in step 306, a different brine fluid may be tested so as to allow measurement of another contact angle in the presence of the additional brine fluid. For example, the control system 145 may open valve 140a and allow the brine fluid 117 in the test cell 105 to begin to drain into the output tank 130. Simultaneously, or soon thereafter, the control system 145 may operate the pump 125 to circulate a different brine fluid 117 (different than what was circulated in step 304) into the test cell 105. Thus, an initial volume of brine fluid may be displaced with another volume of brine fluid.

Method 300 may continue with step 310, which includes controlling the displacement of the initial brine fluid 117 with another brine fluid 117 (for example, by the control system 145) according to a measured property of the brine fluid 117 being displaced (and circulated out of the test cell 105). For example, the sensor 135 may measure values for a particular property of the displaced brine fluid 117, such as, for example, conductivity, salinity, or another property. Such measured values may be sent to the control system 145 from the sensor 135. The control system 145 may compare the measured values to a known (or measured) value of the same property of the displacing brine fluid 117.

Method 300 may continue at step 312, which includes a determination of whether the measured property (for example, conductivity) of the displaced brine fluid matches the known or measured same property of the displacing brine fluid. For instance, when the measured value of the property of the displaced brine fluid 117 matches (or substantially matches, within 1%) the known value of the property of the displacing brine fluid 117, the control system 145 may close the valve 140a (to stop the outflow of the displaced brine fluid 117) and stop the flow of the displacing brine fluid 117 from the tank 120 to the test cell 105. Thus, if the determination in step 312 is no, then method 300 continues at step 308, where additional brine fluid is displaced from the test cell with the other brine fluid. If the determination is yes, then method 300 continues to step 314.

Step 314 includes measuring a contact angle between the hydrocarbon fluid sample and a surface of the rock sample in presence of the other brine fluid. For example, once the measured value of the property of the displaced brine fluid 117 matches (or substantially matches, within 1%) the known value of the property of the displacing brine fluid 117, thereby ensuring that the hydrocarbon fluid sample 102 disposed on the rock sample 110 is in contact with the displacing brine fluid 117. The contact angle between the hydrocarbon fluid sample 102 and the rock sample 110 (in fluid contact with the displacing brine fluid 117) may then be measured.

Method 300 may continue at step 316, which includes determining a wettability alteration of rock sample based on one or more (or both, or more than two) of the measured contact angles. Thus, in some aspects, the different brines may effectively alter the wettability of the rock sample in the test cell.

Method 300 may continue at step 318, which includes a determination of whether another brine fluid (for example, a third brine fluid, a fourth brine fluid, and so on) is to be tested. For example, if multiple (for example, more than two) brine fluids 117 are to be tested, then method 300 may continue back at step 308. Otherwise, method 300 may end.

Figure 4:
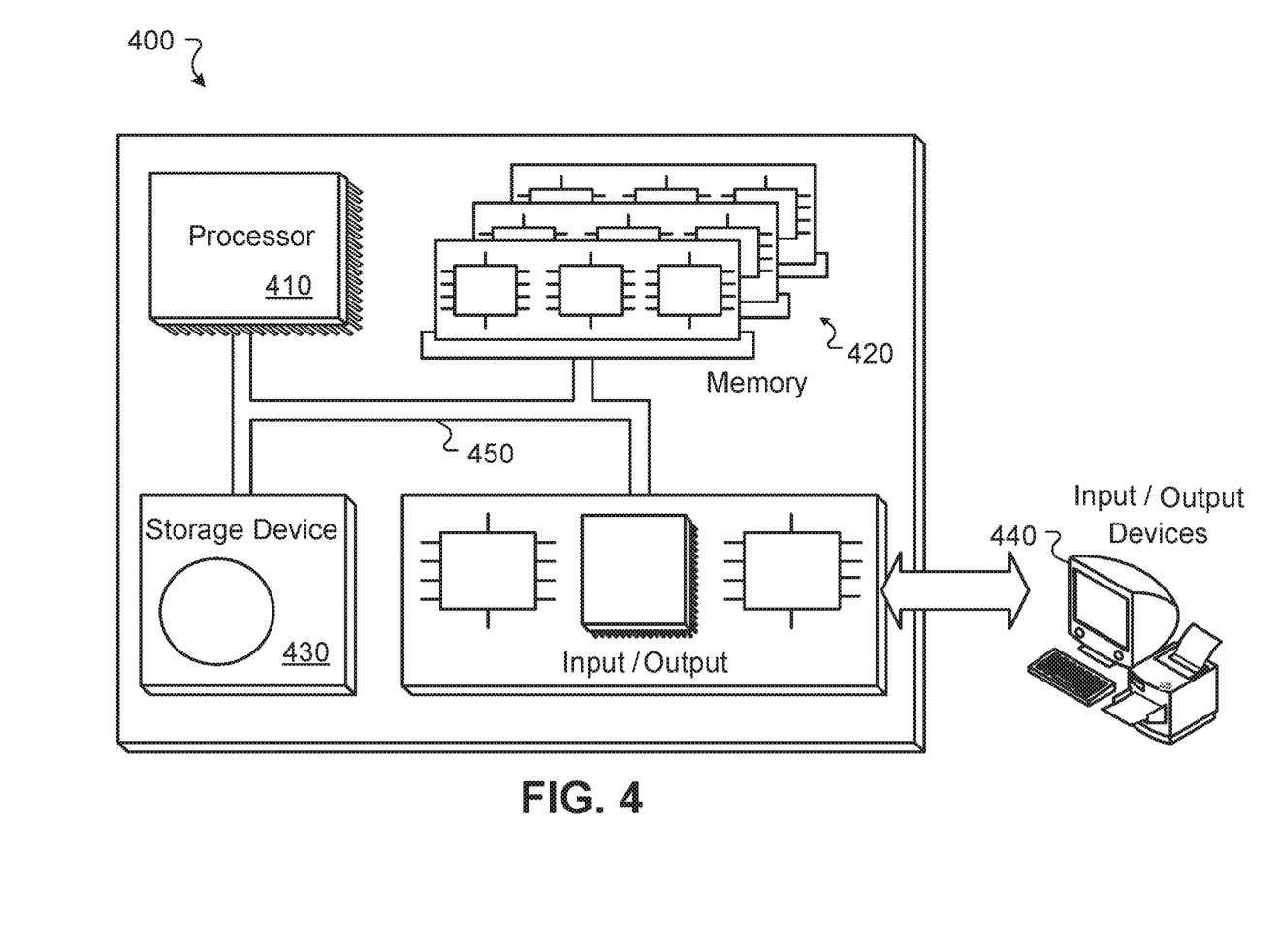
FIG. 4 is a schematic illustration of an example controller for a contact angle measurement system according to the present disclosure.

FIG. 4 is a schematic illustration of an example controller 400 (or control system) for a contact angle measurement system. For example, the controller 400 can be used for the operations described previously, for example as or as part of a control system that performs one or more steps of method 300 described in FIG. 3. For example, the controller 400 may be communicably coupled with, or as a part of, the control system 145 shown in FIG. 1.

The controller 400 is intended to include various forms of digital computers, such as printed circuit boards (PCB), processors, or digital circuitry. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 400 includes a processor 410, a memory 420, a storage device 430, and an input/output device 440. Each of the components 410, 420, 430, and 440 are interconnected using a system bus 450. The processor 410 is capable of processing instructions for execution within the controller 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the controller 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the controller 400. In one implementation, the storage device 430 is a computer-readable medium. In various different implementations, the storage device 430 may be a floppy disk device, a hard disk device, an optical disk device, or a tape device.

The input/output device 440 provides input/output operations for the controller 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A system, comprising:
a test cell configured to enclose a rock sample and a hydrocarbon fluid disposed on a surface of the rock sample;
a first brine fluid tank configured to hold a volume of a first brine fluid, the first brine fluid having a property at a first value;
a second brine fluid tank configured to hold a volume of a second brine fluid, the second brine fluid having the property at the second value;
at least one pump fluidly coupled to the test cell and the first and second brine fluid tanks; and
a control system communicably coupled to the pump and configured to perform operations comprising:
controlling the at least one pump to circulate the first brine fluid into the test cell to contact the rock sample and the hydrocarbon fluid with the first brine fluid;
measuring a first contact angle between the rock sample and the hydrocarbon fluid in contact with the first brine fluid;
controlling the at least one pump to circulate the second brine fluid into the test cell to displace at least a portion of the first brine fluid in the test cell and contact the rock sample and the hydrocarbon fluid with the second brine fluid;
while displacing the first brine fluid with the second brine fluid, controlling the at least one of the at least one pump or at least one valve to circulate an output flow from the test cell, the output flow comprising at least one of the first brine fluid or the second brine fluid;
measuring a salinity of the output flow while circulating the output flow from the test cell;
comparing the measured salinity of the output flow with a known salinity of the second brine fluid;
controlling at least one of the at least one pump or the at least one valve to stop the circulation of the output flow from the test cell when the measured salinity of the output flow matches the known salinity of the second brine fluid;
measuring a second contact angle between the rock sample and the hydrocarbon fluid in contact with the second brine fluid; and
determining a wettability alteration of the rock sample based on at least one of the measured first contact angle or the measured second contact angle.

2. The system of claim 1, wherein the operation of determining the wettability alteration of the rock sample based on at least one of the measured first contact angle or the measured second contact angle comprises determining the wettability of the rock sample based on the measured first contact angle and the measured second contact angle.

3. The system of claim 2, wherein the operation of determining the wettability alteration of the rock sample based on the measured first contact angle and the measured second contact angle comprises determining the wettability of the rock sample based on a difference between the measured first contact angle and the measured second contact angle.

4. The system of claim 3, wherein the property is conductivity, and the hydrocarbon fluid comprises oil.

5. The system of claim 4, wherein the first and second values are different.

6. The system of claim 3, wherein the control system is configured to perform operations further comprising:
controlling the at least one pump to circulate a third brine fluid into the test cell to at least partially displace the second brine fluid with the third brine fluid in the test cell to contact the rock sample and the hydrocarbon fluid with the third brine sample, the third brine fluid having the property at a third value;
measuring a third contact angle between the rock sample and the hydrocarbon fluid in contact with the third brine fluid; and
determining the wettability alteration of the rock sample based on at least one of the measured first contact angle, the measured second contact angle, or the measured third contact angle.

7. The system of claim 6, wherein the operation of determining the wettability alteration of the rock sample based on at least one of the measured first contact angle, the measured second contact angle, or the measured third contact angle comprises determining the wettability of the rock sample based on the measured first contact angle, the measured second contact angle, and the measured third contact angle.

8. The system of claim 6, wherein the control system is configured to perform operations further comprising, while displacing the second brine fluid with the third brine fluid, controlling the at least one pump to circulate the output flow from the test cell, the output flow comprising at least one of the second brine fluid or the third brine fluid.

9. The system of claim 8, wherein the control system is configured to perform operations further comprising measuring a salinity of the output flow while circulating the output flow from the test cell.

10. The system of claim 9, wherein the control system is configured to perform operations further comprising comparing the measured salinity of the output flow with a known salinity of the third brine fluid.

11. The system of claim 1, wherein the property is conductivity.

12. The system of claim 1, wherein the hydrocarbon fluid comprises oil.

13. The system of claim 1, wherein the first and second values are different.

14. The system of claim 1, further comprising a third brine fluid tank configured to hold a volume of a third brine fluid, the third brine fluid having the property at the third value.

15. The system of claim 14, wherein the control system is configured to perform operations further comprising:
controlling the at least one pump to circulate the third brine fluid into the test cell to displace at least a portion of the second brine fluid in the test cell and contact the rock sample and the hydrocarbon fluid with the third brine fluid;
measuring a third contact angle between the rock sample and the hydrocarbon fluid in contact with the third brine fluid; and
determining the wettability alteration of the rock sample based on at least one of the measured first contact angle, the measured second contact angle, or the measured third contact angle.

16. The system of claim 15, wherein the operation of determining the wettability alteration of the rock sample based on at least one of the measured first contact angle, the measured second contact angle, or the measured third contact angle comprises determining the wettability of the rock sample based on the measured first contact angle, the measured second contact angle, and the measured third contact angle.

17. The system of claim 15, wherein the control system is configured to perform operations further comprising, while displacing the second brine fluid with the third brine fluid, controlling at least one of the at least one pump or the at least one valve fluidly coupled to the test cell to circulate the output flow from the test cell, the output flow comprising at least one of the second brine fluid or the third brine fluid.

18. The system of claim 17, wherein the control system is configured to perform operations further comprising measuring a salinity of the output flow while circulating the output flow from the test cell.

19. The system of claim 18, wherein the control system is configured to perform operations further comprising comparing the measured salinity of the output flow with a known salinity of the third brine fluid.

20. The system of claim 19, wherein the control system is configured to perform operations further comprising controlling at least one of the at least one pump or the at least one valve to stop the circulation of the output flow from the test cell when the measured salinity of the output flow matches the known salinity of the third brine fluid.

* * * * *